(12) United States Patent
Loibner et al.

(10) Patent No.: US 7,615,226 B2
(45) Date of Patent: Nov. 10, 2009

(54) METHOD FOR PRODUCING VACCINES CONTAINING A HEAT-TREATED MIXTURE CONSISTING OF AT LEAST ONE ANTIGEN AND OF AT LEAST ONE ADJUVANT

(75) Inventors: Hans Loibner, Vienna (AT); Helmut Eckert, Oberwil (CH)

(73) Assignee: Dr. Hans Loibner, Vienna (AT)

( * ) Notice: Subject to any disclaimer, the term of this patent is extended or adjusted under 35 U.S.C. 154(b) by 241 days.

(21) Appl. No.: 10/220,298

(22) PCT Filed: Mar. 21, 2001

(86) PCT No.: PCT/AT01/00080

§ 371 (c)(1),
(2), (4) Date: Sep. 12, 2002

(87) PCT Pub. No.: WO01/70264

PCT Pub. Date: Sep. 27, 2001

(65) Prior Publication Data

US 2003/0143221 A1    Jul. 31, 2003

(30) Foreign Application Priority Data

Mar. 21, 2000    (AT)    ............... A 472/2000

(51) Int. Cl.
*A61K 39/00*    (2006.01)
(52) U.S. Cl. ............... 424/184.1; 424/201.01; 424/278.1
(58) Field of Classification Search ............... 424/184.1
See application file for complete search history.

(56) References Cited

U.S. PATENT DOCUMENTS 3,876,763 A * 4/1975 Yoshikazu et al. ....... 424/201.1
5,370,871 A * 12/1994 Dintzis et al. ............ 424/244.1
6,270,723 B1 * 8/2001 Laugharn et al. ............... 422/39
6,818,222 B1 * 11/2004 Barchfeld et al. ........ 424/236.1

FOREIGN PATENT DOCUMENTS

| EP | 0 159 748 | 10/1985 |
| WO | 98 56419 | 12/1998 |
| WO | 00 41722 | 7/2000 |
| WO | 01 35989 | 5/2001 |

OTHER PUBLICATIONS

Kuby, Immonology, Ed. 4, W.H. Freeman and Co., Chapter 18, pp. 449-465.*
Burrell et. al. Vaccine, Stability of aluminum containing adjuvants to autoclaving, vo. 17., pp. 2599-2603).*
Letvin NL, Annu Rev Med 2005, Feb., pp. 213-223.*
Spitler, Cancer Biotherapy, 1995, v.10, pp. 1-3.*
Ezzell, NIH Research, 1995 vol. 7, p. 46-49.*
P. Cooper et al.: "Algammulin, a new vaccine adjuvant comprising gamma inulin particles containing alum: preparation and in vitro properties" Vaccine, vol. 9, No. 5, pp. 351-357 May 1991.
J. Kreuter: "Nanoparticle-based drug delivery system" Journal of Controlled Release, vol. 16, No. 1-2, pp. 169-176 Jun. 1991.
K. Speidel et al.: "Priming of cytotoxic T lymphocytes by five heat-aggregated antigens in vivo: conditions, efficiency, and relation to antibody responses" European Journal of Immunology, vol. 27, No. 9, pp. 2391-2399 Sep. 1997.

* cited by examiner

*Primary Examiner*—Michael Szperka
*Assistant Examiner*—Yunsoo Kim
(74) *Attorney, Agent, or Firm*—Oblon, Spivak, McClelland, Maier & Neustadt, L.L.P.

(57) ABSTRACT

A method of preparing a vaccine formulation comprising at least one antigen and at least one adjuvant is described, which method is characterized in that at least one antigen is mixed with at least one adjuvant and the mixture subsequently is heat-treated at a temperature of at least 80° C. for a period of time of at least 5 minutes.

12 Claims, 1 Drawing Sheet

Figure 1:
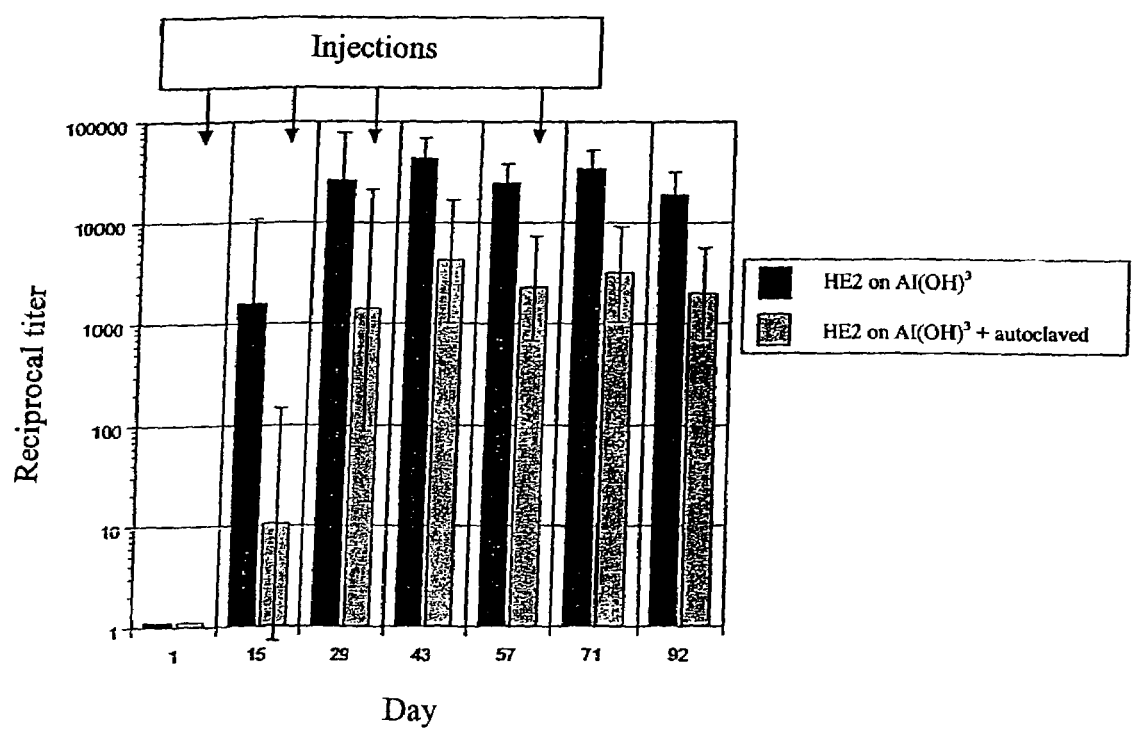

METHOD FOR PRODUCING VACCINES CONTAINING A HEAT-TREATED MIXTURE CONSISTING OF AT LEAST ONE ANTIGEN AND OF AT LEAST ONE ADJUVANT

The present invention relates to a method of preparing vaccines which comprise at least one antigen and at least one adjuvant.

World-wide, the protective immunization is among the most efficient and successful achievements of modern medicine. Active and passive immunization of humans and animals against various diseases are used to efficiently fight world-wide diseases and deaths caused by former "scourges of humanity". Particularly the active immunization in which bacterial or viral antigens incapable of reproduction are administered can be viewed as the most efficient method for a world-wide prevention of such diseases.

Since upon a vaccination, the antigens selected for a vaccination by themselves frequently trigger merely slight or insufficient immune responses in the organism itself, by which no real protection against the disease is formed, usually also immunostimulating auxiliary agents are provided in a vaccine formulation, in addition to the active substance triggering the immune response. Therefore, nearly all the common vaccines contain so-called adjuvants with which the immune response to certain specific antigens is to be improved. Thus, the immune response induced by vaccines can be markedly improved for instance by a binding to certain adjuvants, such as aluminum hydroxide.

In the course of the present invention it has, however, been shown that the binding of the antigens, in particular of polypeptide-based antigens, to such adjuvants is instable and unspecific, so that immediately after the administration of such vaccine formulations, the antigen largely becomes detached from the adjuvant, and only a small percentage of specific antigen remains on the adjuvant.

Therefore, it is an object of the present invention to provide improved vaccine formulations which are capable of triggering a changed connection between antigen and such an adjuvant, and thus an improved immune response.

The invention is directed to a method of preparing a vaccine formulation, comprising at least one antigen and at least one adjuvant, which is characterized in that at least one antigen is mixed with at least one adjuvant and said mixture subsequently is heat-treated in solution or suspension at a temperature of at least 80° C. for a period of time of at least 5 minutes. It has been shown that during this process, the adhesion of the antigens to the adjuvant is decisively changed so that upon introduction of the vaccine prepared according to the invention into the individual to be immunized (human/animal) there will be no immediate exchange of the immunoantigen with the proteins present at the site of administration.

As the antigens, according to the invention preferably polypeptide-based antigens are used, i.e. peptide antigens, or proteinaceous antigens, respectively. Such peptide antigens have lengths from about 6 amino acids onwards (e.g. 8 to 11 amino acids), yet they may also consist of much longer polypeptide chains, comprising, e.g., the entire native antigenic protein or the respective antigenic protein sub-units or parts or derivatives thereof.

In principle, the protein antigen contained in the mixture may be any desired protein that can be used as an antigen for a vaccination. With proteins, in the present invention polypeptides of more than five amino acids are to be understood which may additionally comprise other substances covalently bound in the molecule structure (such as, e.g., sugars, lipids, phosphate groups). The side groups are not limited to natural polypeptide modifications, but may also be artificial modifications (such as, e.g., polyethylene glycol). In a preferred embodiment of the method according to the invention, the protein antigen is an antibody.

The antigens of the present invention are not limited to certain antigens, so that viral antigens (e.g. against HAV, HBV, HCV or HIV) and bacterial antigens may be used according to the invention just like allergens, tumor antigens or antigens from eukaryotic pathogens. Here also complete virus particles, bacteria or fragments thereof can be used as antigens.

As adjuvants, according to the invention surface-active solids may be used on which antigens can adsorb. Particularly preferred adjuvants used within the scope of the present invention are aluminum-based adjuvants, e.g. aluminum phosphate, and in particular aluminum hydroxide which has generally proven to be suitable as a vaccine adjuvant.

It has been shown that with the present invention, despite the use of relatively high temperatures on the combination of adjuvant and antigen in suspension or solution, even complex antigens are not or merely un-significantly changed in their antigenic potential so that also sensitive, instable antigenic protein structures can be used in vaccine formulations according to the invention.

According to the invention it has been shown that the heat treatment must be effected at least at a temperature of 80° C. so as to obtain the inventive effects. This also explains why the inventive effect does not occur in a conventional pasteurisation which is mostly effected at around 65° C. In the heat treatment, the use of temperatures of from 90° C. to 130° C., in particular of from 100° C. to 125° C., has proven particularly suitable, as well as (at temperatures above the boiling point of the solution at normal pressure) the use of closed systems, such as autoclaves or other pressure containers, with pressures above atmospheric then being used.

It is found that at higher temperatures also shorter treatment times than in conventional pasteurising (with certain proteins which exhibit rapid binding to the adjuvant at high temperatures, even less than 5 min) can be provided so that the heat treatments preferably can be carried out during 20 to 200 min, in particular during 30 to 60 min (particularly at higher temperatures). In the routine process, the vaccine formulations usually are heated at 121° C. for 30 min. When lowering the treatment temperature per 10° C., the duration of heating will usually be doubled.

A "side effect" of the present invention is that during the heat treatment also potentially present pathogens, in particular human pathogenic viruses, can be successfully inactivated. Since due to the presence of adjuvants, temperatures of more than 80° C. can be provided without a decisive deterioration in the antigen structure occurring, according to the invention a vaccine decisively improved in terms of its virus safety, or a vaccine which comprises a markedly lower portion of denatured components, respectively, can be provided.

Although at the temperatures to be provided according to the invention, proteins in solution usually become irreversibly denatured, the antigen/adjuvant mixture according to the present invention surprisingly substantially retains its immunogenic properties and can still be used as an effective vaccine.

By the heat treatment and the associated improved fixation to the adjuvant, the preparation prepared according to the invention has decisive advantages as regards its production as well as its storage and distribution. The advantage of the higher virus safety plays a crucial role particularly also for protein antigens derived from human or animal material. Due to the method according to the invention and the sterilisation effected thereby, it is possible to carry out the heat treatment and also the subsequent packaging steps without preservatives or stabilizers. When applying the method according to the invention to vaccines that have already been filled into containers, the sterilisation occurring thereby makes it possible to do without preservatives, such as, e.g., thimerosal, in the formulation.

Within the scope of the present invention, the term "vaccine" means an agent for active immunization, i.e. an induction of a specific immune response by administering (e.g. subcutaneously, intradermally, intramuscularly, possibly also orally, intranasally) small amounts of an antigen (a substance recognized as foreign and, thus immunogenic, by the immune system of the vaccinated individual) in a suitable immunogenic formulation. Thus, the antigen is used as a "trigger" for the immune system so as to build up an immune response specific for the antigen. The amounts of antigen required therefor may basically be very small (some vaccines contain only approximately 5-10 µg of antigen per vaccination dose). A dose-response curve which in large areas is only little dependent on amounts is characteristic of an active immunization. This means that the immune response will be approximately equally high in a wide range of doses. Hence follows that with a vaccination, the desired effect, i.e. the induction of an immune response, can already be achieved with very small amounts of antigen, yet it can also be achieved in a comparable manner with substantially higher amounts of antigen. Yet, naturally, it is desirable basically to work with as low doses as possible, particularly with a view to side effects, costs of material etc., which play a role in vaccination.

Vaccines may be used for various purposes: for establishing an immune status of the vaccinated persons or animals such as will protect them against pathogenic microorganisms, such as, e.g., certain viruses or bacteria. This also includes vaccines against cancer. In this instance, the immune system of cancer patients shall be selectively activated to fight malignant cells. This has been attempted by the most varying approaches. A novel method of cancer vaccination has been described in application PCT/EP00/00174. The monoclonal antibody HE2 described therein which is used as a vaccine antigen in a cancer vaccination, serves as an example, without being limited thereto, for the formulation of a vaccine according to the method described here.

A vaccine as defined by the present invention may basically be used both for therapeutical purposes and also prophylactically (as it is with all anti-microbial vaccines).

The present invention also relates to a vaccine formulation obtained or obtainable by the method according to the invention. What has been said above in connection with the method according to the invention also applies to the preferred embodiments of this vaccine formulation.

With the present invention human vaccine formulations with (against) proteins can be particularly effectively prepared, from which it has been believed so far that they do not withstand heat treatments as such high temperatures as provided according to the invention. Yet precisely for these proteins, the combined heat treatment in the presence of adjuvants seems to have no or merely an insignificant adverse effect on their immunostimulating properties, at least the functional immune response, i.e. the desired protective action, remains unaffected by the heat treatment according to the invention.

As has already been mentioned, one of the decisive advantages of this vaccine formulation resides in the changed adhesion or binding of the antigen to the adjuvant, so that this bond is no longer measurably released upon administration to an individual being vaccinated, even if there is an excess of other proteins at the site of administration. In conventional antigen/ adjuvant formulations it has been shown—as shown in the following Examples—that it takes only approximately 1 min until nearly all the antigen in the organism to be vaccinated is no longer present in a form connected to the adjuvant. This can successfully be prevented by the vaccine according to the invention so that a substantially slower desorption from the adjuvant will occur. The vaccine treated according to the invention exhibits a desorption of the antigen from the adjuvant improved (=slowed) by at least 50%, preferably at least 90%, in particular at least 99% relative to the non-treated vaccine (measured e.g. 10 min or 1 h after introduction of the vaccine formulation in 2% fetal calf serum).

The invention will be explained in more detail by way of the drawing as well as by way of the following Examples to which, of course, it shall not be restricted.

FIG. 1 shows the immune response which can be caused in monkeys by a heat-treated antibody vaccine (cf. Example 1).

EXAMPLES

Example 1

Heat-Sterilized Formulation of the Monoclonal Antibody HE2 on Aluminum Hydroxide 0.5 mg of HE2 (mouse monoclonal antibody $IgG_2a$), absorbed on 1.67 mg of aluminum hydroxide in 0.5 ml 1 mM phosphate buffer, pH 6,0/155 mm NaCl, was heated for 30 min at 121° C. Four rhesus monkeys were each immunized subcutaneously with this dose at days 1, 15, 19 and 57. The sera of various points of time were tested by means of ELISA for an induction of antibodies against HE2. As comparison, the same formulation, yet without heat treatment, was inoculated and also analyzed (FIG. 1). It can be seen that with the heat-treated vaccine hardly lower titers have been produced against the protein antigen.

The following table shows the reduced desorption of the heat-treated vaccine formulation as compared to an untreated formulation:

The serum of immunized monkeys (4 individual each) were tested in ELISA for HE2 present therein. Affinity-purified goat-anti-HE2 serum was immobilized on the ELISA plates. In various dilutions with anti-human-1gG-peroxidase conjugate, the sera were tested for specific antibodies. The sensitivity of the test was at 10 ng of HE2/ml. The samples were drawn before the first imminization as well as 1, 4 and 24 h after the immunization. As an external quantitative standard, HE2 was used. It can be seen that the heat-treated vaccine formulation did not cause any measurable HE2 level in the blood, whereas the non-heat-treated vaccine formulation releases a large portion of the HE2 into the serum within 24 h.

| Point of Time | Heat-Treated Vaccine | Non-treated Vaccine |
| --- | --- | --- |
| 0 | 0; 0; 0; 0 ng/ml | 0; 0; 0; 0 ng/ml |
| 1 h | 0; 0; 0; 0 ng/ml | 13; 17; 74; 280 ng/ml |
| 4 h | 0; 0; 0; 0 ng/ml | 200, 280, 400, 740 ng/ml |
| 24 h | 0; 0; 0; 0 ng/ml | 960, 960, 1000, 740 ng/ml |

Example 2

Heat-Treatment of a Hepatitis B Vaccine

EngerixB (SmithKline Beecham; 0.20 µg/ml) was filled into small puncturable bottles and heat-treated at 121° C. for 30 min.

The immunogenicity of the thus treated vaccine was tested in mice. For this purpose, 8 mice each (Him:OF1, female; 20 to 25 g live weight) were immunized with the heat-treated and with the non-heat-treated vaccine, respectively, (0.155 ml, i.p.), a further control group was not immunized. After 2 weeks, blood was drawn from the mice, and the hepatitis-specific titer was determined.

For this purpose, 96 well ELISA plates (MaxiSorp, Nunc, Denmark) were coated with recombinant HBs antigen, adr sub-type (Fitzgerald Industries Inc., USA) (10 µg/ml coating buffer; duration: over night, at 4° C.). After washing, dilution series of the sera of the individual mice (in washing buffer) were applied and incubated at room temperature for 8 h. After re-washing, it was incubated with anti-mouse-immunoglobulin peroxidase conjugate (Sigma, USA) in corresponding dilution at room temperature (2 h). After re-washing the plates, substrate was added, staining was stopped after 30 min, and it was measured in the photometer at 492 nm.

The relative titer increase was determined by comparing the titer of the two vaccine groups with the titer of the non-vaccinated mice. It has been shown that the relative titer increases in the two vaccination groups were equally high.

Material:
Coating buffer: 15 mM $Na_2CO_3$, 35 mM $NaHCO_3$, 3 mM $NaN_3$, pH: 9.6
PBS: 138 mM NaCl; 1.5 mM $KH_2PO_4$; 2.7 mM KCl; 6.5 mM $Na_2HPO_4$; pH: 7.2
Washing buffer: 0.05% Tween 20 in PBS
Staining buffer: 24.3 mM citric acid; 51.4 mM $Na_2HPO_4$; pH: 5.0
Substrate: 40 mg o-phenylene diamine dihydrochloride; 100 ml staining buffer; 20 1 µl $H_2O_2$ (30%)
Stop solution: 4 N $H_2SO_4$

Example 3

Study Regarding the Adsorption and Desorption Behavior of the Antigen on Alu Gel The HE2 formulations described in Example 1 (heat-denatured and non-heat-denatured) are studied in a displacement test:

The suspension of the vaccines was centrifuged off; the supernatant was tested in an ELISA for the presence of the antigen (specific mouse-immunoglobulin (HE2)). In the supernatant of the non-heat-treated vaccine, 0.1% of the entire formulated antibody amount could be detected, in the supernatant of the heat-denatured vaccines no antigen could be detected.

The vaccines which had been centrifuged off were each slurried in PBS plus 2% of FCS (fetal calf serum) and shaken at 37° C. for 1 h.

Subsequently, it was centrifuged off again, and the respective supernatants were tested in the above-mentioned ELISA. In the supernatant of the non-heat-treated vaccines, more than 95% of the entire formulated antibody amount could be detected, in the supernatant of the heat-denatured vaccines, again no antigen could be detected.

The tests and results indicated in this Example show that in the vaccine formulation prepared according to the method of the invention, the antigen (under physiological conditions) is irreversibly bound to the adjuvant.

ELISA:

Unless stated otherwise, the ELISA was carried out according to common methods.

The incubation times are 30 min for coating, 1 h for all other steps (samples; conjugate), each at 37° C. The volumes used are 100 µl per well in all the steps, except for the blocking (200 µl per well).

For coating the ELISA plates, a polyclonal goat-anti-HE2 antibody (IGN111) is used which had been purified by immunoaffinity chromatography. Coating concentration (10 g/ml coating buffer).

HE2 serves as the standard (Mouse IgG 2a, kappa) (10 mg/ml in phosphate-buffered saline; pH=6.0).

Dilution series in PBS with 2% FCS were prepared both from the standard and from the samples, and the individual dilutions were applied.

For the detection of HE2 bound to IGN111 from the sample dilutions and the standard dilutions, HRP (horseradish peroxidase)-anti-mouse IgG2a (Zymed, USA) was used as enzyme conjugate.

After the enzyme substrate staining, the reaction was stopped with sulfuric acid, and staining was measured at 492 nm.

For the quantitative evaluation, the dilution series of the samples were accordingly compared with the dilution series of the standard (HE2).

Material:
Washing buffer:

| | |
|---|---|
| NaCl | 21.2 g |
| TritonX-100 | 2.5 ml |
| PBS | ad 1000.0 ml |

Coating buffer:

| | |
|---|---|
| $Na_2CO_3$ | 1.59 g |
| $NaHCO_3$ | 2.93 g |
| Aqua dest. | ad 1000.0 ml |
| pH = 9.6 | |

Staining buffer:

| | |
|---|---|
| Citric acid | 5.6 g/l |
| di-$Na_2HPO_4 \times 2H_2O$ | 9.15 g/l |
| Aqua dest. | ad 1000.0 ml |
| pH = 5.0 | |

PBS:

| | |
|---|---|
| NaCl | 8.0 g/l |
| $KH_2PO_4$ | 200.0 mg/l |
| KCl | 200.0 mg/l |
| $Na_2HPO_4$ | 1.44 g/l |
| Aqua dest. | ad 1000.0 ml |
| pH = 7,2 | |

FCS (Fetal Calf Serum):
 heat-inactivated (1 h at 56° C.),
 Gibco Life Technologies Cat. No. 10270-106
Substrate solution: 1 o-phenylene diamine dihydrochloride tablet (Sigma, P-8287) per 10 ml staining buffer plus 60 µl $H_2O_2$ 30% (Merck 1.08597.1000).
$H_2SO_4$ 30%: Fluka, 84724
ELISA plate: F 96 Maxisorp, Nunc-Immuno Plate, Nunc Brand Products, 442404

The invention claimed is:

1. An immunogenically active vaccine formulation comprising a mixture formed by at least one antigen and at least one adjuvant, said mixture having been subjected to a heat treatment at a temperature of from 100° C. to 125° C. for a period of time of at least 5 minutes, said at least one antigen thereby having an improved adhesion on said at least one adjuvant,
 wherein the antigen is a polypeptide and the adjuvant is an aluminum hydroxide.

2. The vaccine as set forth in claim 1, wherein at least one antibody is used as said at least one antigen.

3. The vaccine as set forth in claim 2, wherein said at least one antibody is at least one monoclonal antibody.

4. The vaccine as set forth in claim 1, wherein several antigens having different specificities are mixed with said at least one adjuvant.

5. The vaccine as set forth in claim 2, wherein antibodies having different specificities are mixed as said antigens with said at least one adjuvant.

6. The vaccine as set forth in claim 2, wherein said at least one antibody mixed as an antigen with said at least one adjuvant is selected from the group consisting of HE2 and an antibody having the same binding specificity as HE2.

7. The vaccine as set forth in claim 1, wherein said heat treatment is carried out for a period of time of from 20 and 200 minutes.

8. The vaccine as set forth in claim 1, wherein said heat treatment is carried out for a period of time of from 30 and 60 minutes.

9. The vaccine as set forth in claim 1, wherein the antigen is a monoclonal antibody.

10. The vaccine as set forth in claim 1, wherein the antigen is HE2.

11. The vaccine as set forth in claim 1, wherein the antigen is an antibody having the same binding specificity as HE2.

12. The vaccine as set forth in claim 1, in the form of a suspension.

* * * * *